(12) United States Patent
Druzgala

(10) Patent No.: US 6,686,377 B2
(45) Date of Patent: Feb. 3, 2004

(54) ULTRASHORT-ACTING OPIOIDS FOR TRANSDERMAL APPLICATION

(75) Inventor: Pascal Druzgala, Santa Rosa, CA (US)

(73) Assignee: ARYx Therapeutics, Santa Clara, CA (US)

( * ) Notice: Subject to any disclaimer, the term of this patent is extended or adjusted under 35 U.S.C. 154(b) by 0 days.

(21) Appl. No.: 10/116,320

(22) Filed: Apr. 3, 2002

(65) Prior Publication Data

US 2002/0183343 A1 Dec. 5, 2002

Related U.S. Application Data

(60) Provisional application No. 60/281,080, filed on Apr. 3, 2001.

(51) Int. Cl.[7] .................... A61K 31/445; C07D 211/92
(52) U.S. Cl. ........................................ 514/330; 546/224
(58) Field of Search ........................ 546/224; 514/330

(56) References Cited

FOREIGN PATENT DOCUMENTS

EP          0 383 579 A1       8/1990

OTHER PUBLICATIONS

Lutz et al, Chemical Abstract, vol. 122 No. 23235, "A pharmacodynamic model to investigate the structur–activity profile of a series of novel opioid analgesics", (1994).*

James et al, Journal of Pharmacology an Experimental Therapeutics, vol. 259 No. 2 pp 712–718 "Opioid receptor activity of G 87084B" (1991).*

Feldman, P., et al., "Design, Synthesis, and Pharmacological Evaluation of Ultrashort– to Long–Acting Opioid Analgetics", *Journal of Medicinal Chemistry*, 1991, pp. 2202–2208, vol. 34, No. 7, American Chemical Society.

Database CA [Online] Chemical Abstracts Service, Columbus, Ohio, US; Yang, Yulong et al.: "Anesthetic effect of some 4–substituted fentanyl derivatives in mice" retrieved from STN Database accession No. 130:32672 (abstract) & Huaxi Yaoxue Zazhi (1998), 13(2), 80–82 (abstract).

Lutz, M. et al. (1994) "A pharmacodynamic model to investigate the structure–activity profile of a series of novel opioid analgesics" *Journal of Pharmacology and Experimental Therapeutics* 271(2):795–803, abstract only.

* cited by examiner

*Primary Examiner*—Alan L. Rotman
*Assistant Examiner*—Raymond Covington
(74) *Attorney, Agent, or Firm*—Saliwanchik, Lloyd & Saliwanchik

(57) ABSTRACT

The subject invention concerns novel analogs of fentanyl opioids. The subject invention also concerns methods for synthesizing the compounds of the invention. The invention also concerns methods for treating pain in a patient by administering a compound of the invention to a person in need of such treatment.

19 Claims, 12 Drawing Sheets

Fentanyl

Alfentanyl

Sufentanyl

Remifentanil

Fentanyl

R1 and R2 are independently H or CH$_3$
R$_3$ is methyl, ethyl, isopropyl, ter-butyl, etc.

R= alkyl, for example, methyl, ter-butyl; aryl, for example, phenyl, etc.
$R_1$=H or $CH_3$ (1) Phenethyl bromide, K₂CO₃, acetone. (2) NaCN, aniline. (3) SOCl₂, methanol.
(4) methyl chloroformate, DMAP, Et₃N, CH₂Cl₂. (5) Chloromethylacetate, CH₂Cl₂.

ULTRASHORT-ACTING OPIOIDS FOR TRANSDERMAL APPLICATION

CROSS-REFERENCE TO RELATED APPLICATION

This application claims the benefit of U.S. Provisional Application No. 60/281,080, filed Apr. 3, 2001.

BACKGROUND OF THE INVENTION

Fentanyl is an opioid analgesic that is roughly one-hundred fold more potent than morphine. Chemically, it is a 1,4-disubstituted piperidine molecule with agonist properties at the $\mu$-opioid receptor. This type of receptor is found in the brain as well as in various peripheral tissues and in the spinal chord. A transdermal delivery system for fentanyl has been described. This system delivers fentanyl at rates between 25 and 100 $\mu$g/hour. Due to severe side effects, the fentanyl transdermal system described in the art is indicated only in the management of chronic pain in patients requiring continuous opioid analgesia for pain that cannot be managed by lesser means. Because serious or life-threatening hypoventilation could occur, the use of fentanyl transdermal treatment is strongly contraindicated in children younger than 12 years of age, in the management of acute or post-operative pain, including use in outpatient surgery, and in general in any situation where pain can be managed by non-opioid therapy.

The development of a short-acting transdermal fentanyl analog system would be of great value. A soft fentanyl analog has been described in the art. Remifentanyl (Ultiva®) is marketed by Glaxo Wellcome as an ultrashort acting opioid for intravenous analgesia in anaesthetic cocktails. Due to its high degree of efficiency against extreme pain, a safe soft analog of fentanyl could be used in cases of pain management that are not presently suitable for the current opioid therapy.

BRIEF SUMMARY OF THE INVENTION

The subject invention provides novel analogs of fentanyl opioids. The subject invention also provides methods for synthesizing the compounds of the invention. The invention also concerns methods for treating pain in a patient by administering a compound of the invention to a person in need of such treatment.

DETAILED DISCLOSURE OF THE INVENTION

The subject invention provides novel analogs of fentanyl opioids. Preferably, the opioid analog can be deactivated by hydrolytic enzymes to a primary inactive metabolite. In exemplified embodiments, the piperidine nitrogen or the 4-position of the piperidine ring is modified. Optionally, a positive charge can be introduced on the piperidine nitrogen. Compounds of the present invention can be advantageously used to treat patients suffering from extreme cases of pain that cannot be safely treated using present opioid therapeutics.

The subject invention also concerns methods for synthesizing the compounds of the invention. The chemical structure of the piperidine backbone of the molecule lends itself to the introduction of a positive charge. This positive charge can be made permanent or can be made reversible (prodrug approach). A permanent positive charge affords the advantage that the molecule does not have any central effect, therefore avoiding the risks of hypoventilation regardless of metabolic rate. Alternatively, a reversible positive charge allows for transdermal delivery by iontophoresis of a potent soft fentanyl analog with a short duration of action. By appropriately selecting the half-life of the soft fentanyl analog, it is possible to match the delivery rate of the drug with its clearance rate, thereby minimizing and controlling undesired side effects associated with the drug.

Figure 1:
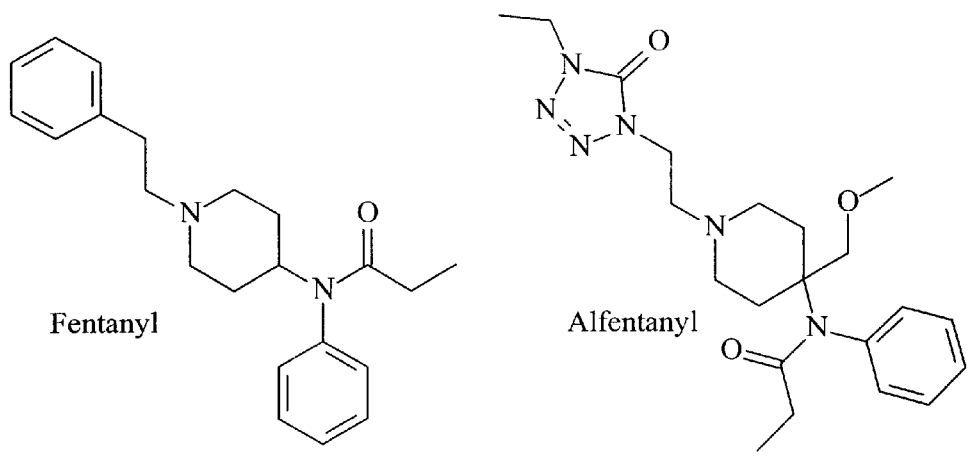
FIG. 1 shows certain opioid analgesics that are marketed in the United States.
Figure 1:
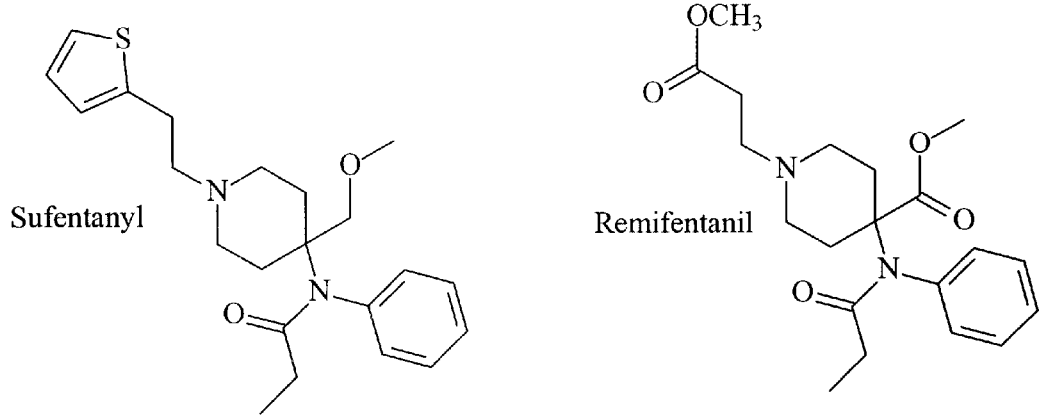
Figure 2:
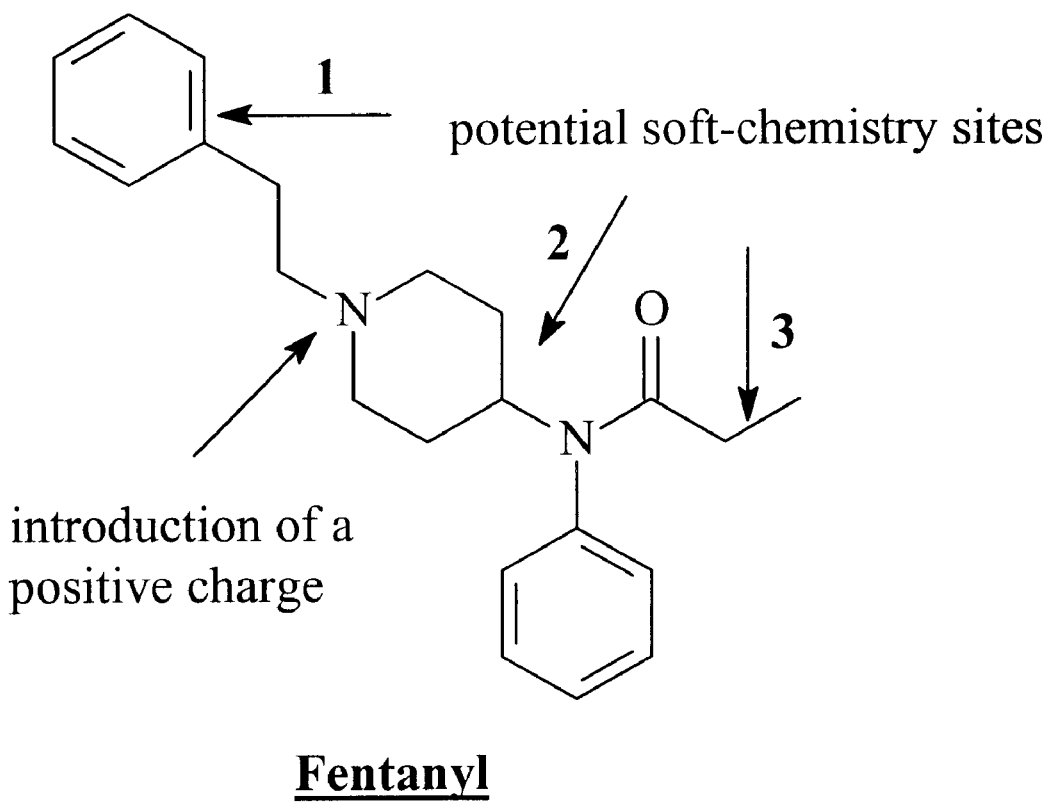
FIG. 2 shows several potential sites for modification of opioid compounds according to the subject invention.
Figure 3:
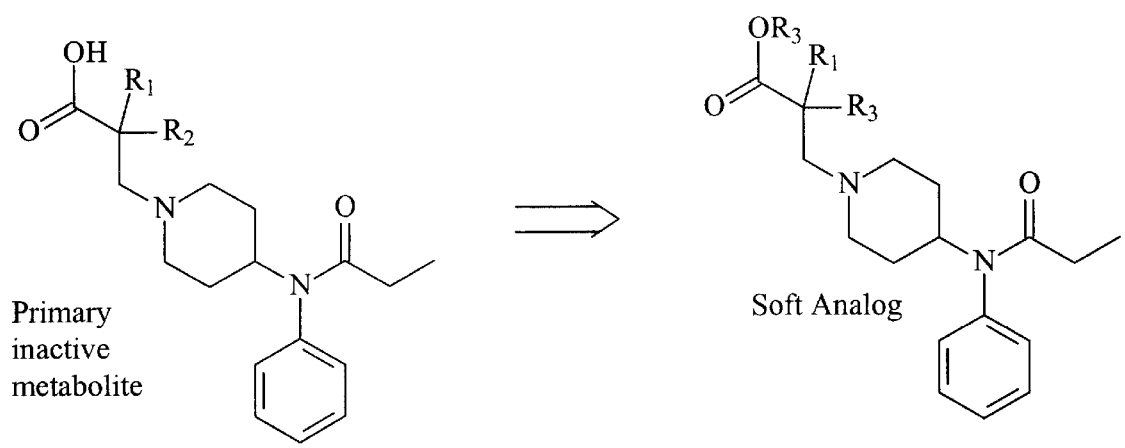
FIGS. 3–8 show compounds of the subject invention.
Figure 4:
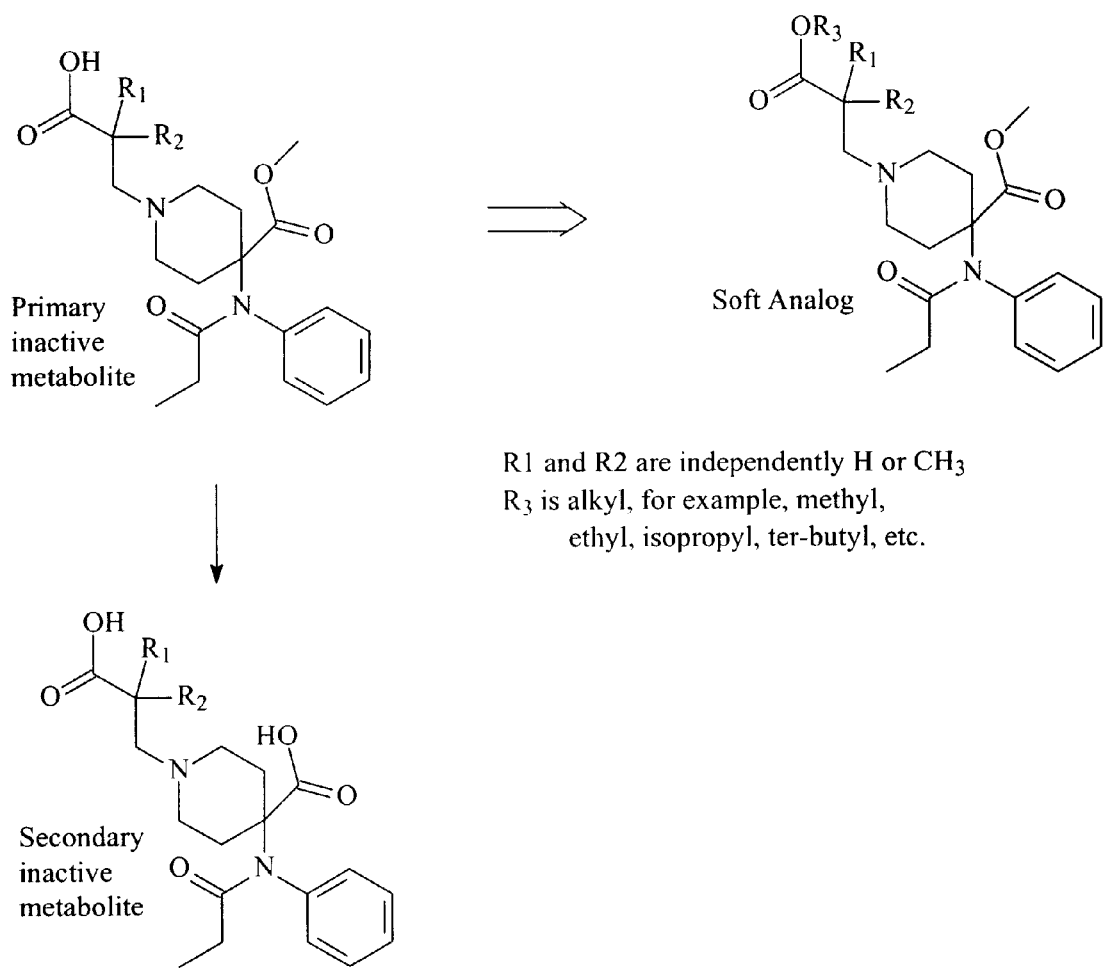
Figure 5:
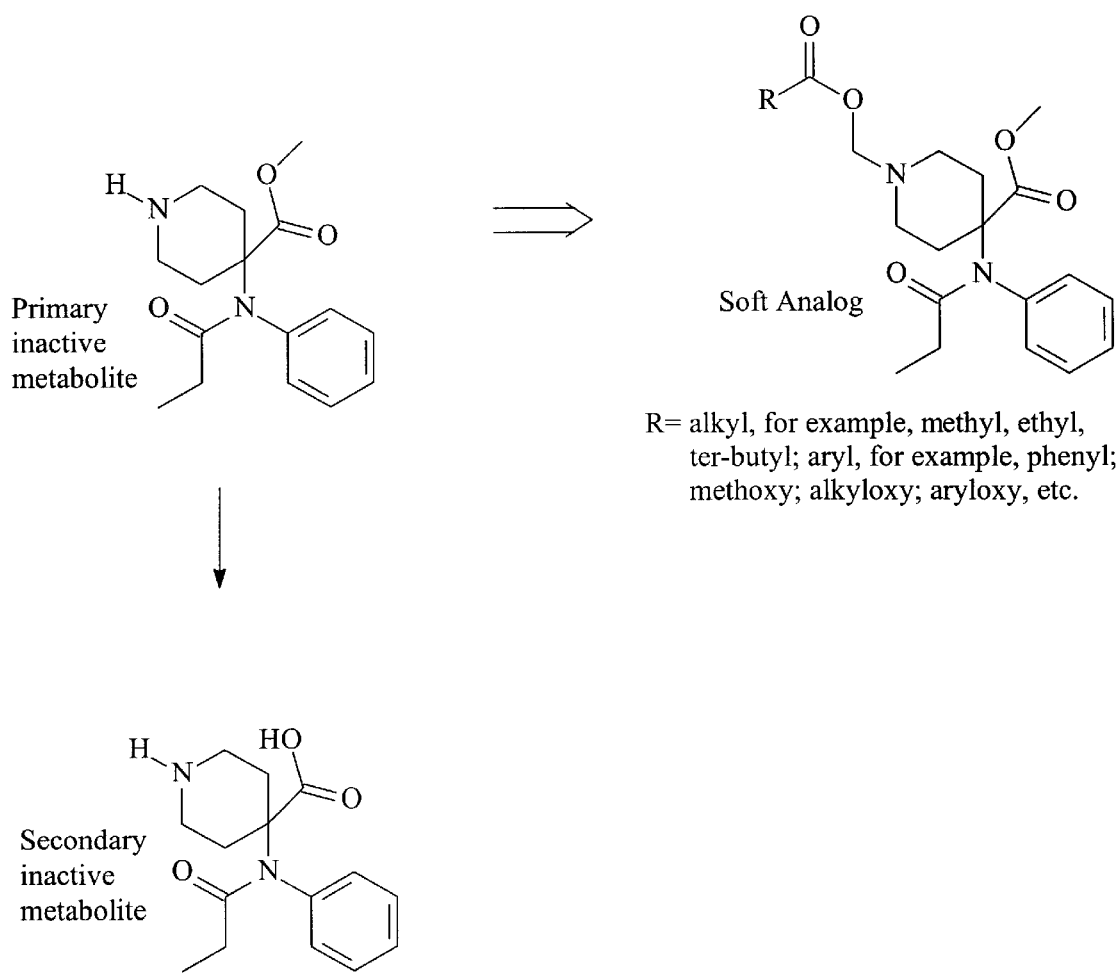
Figure 6:
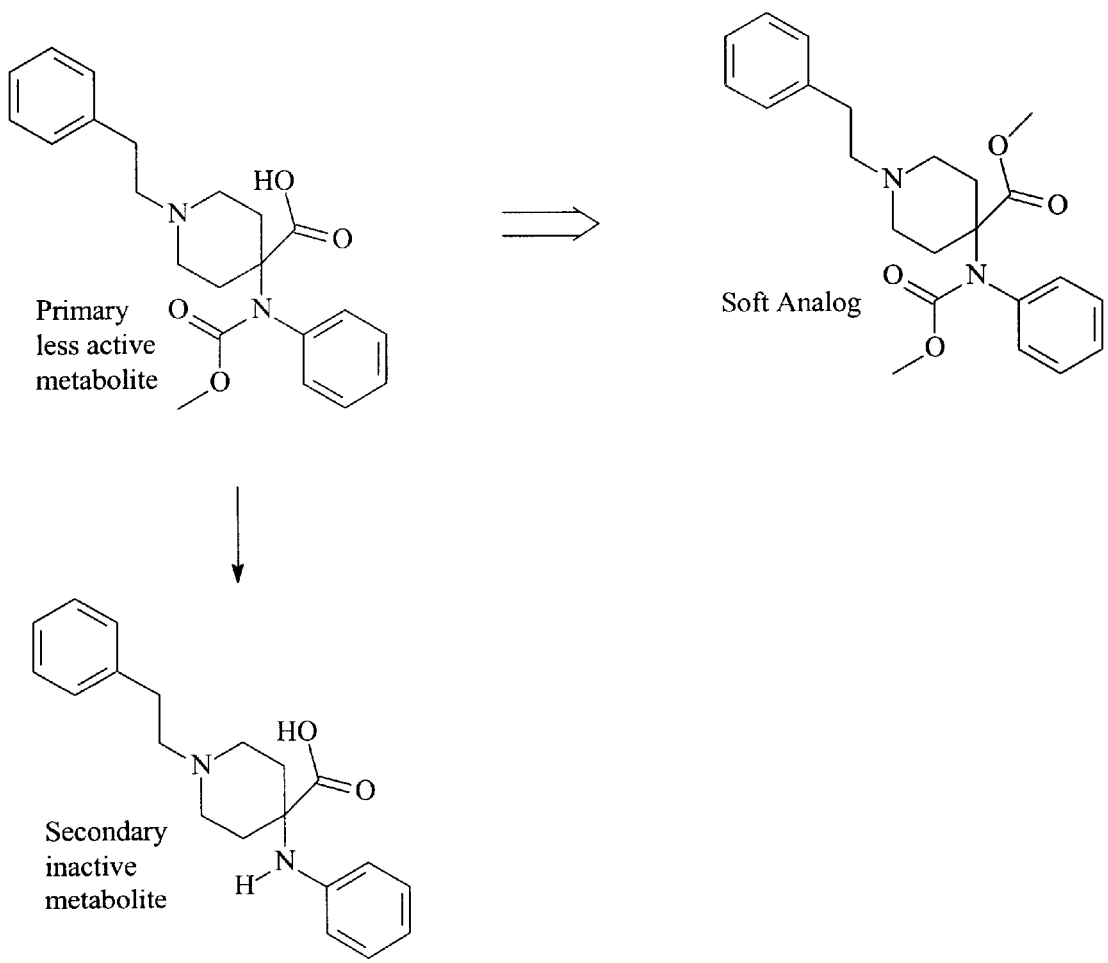
Figure 7:
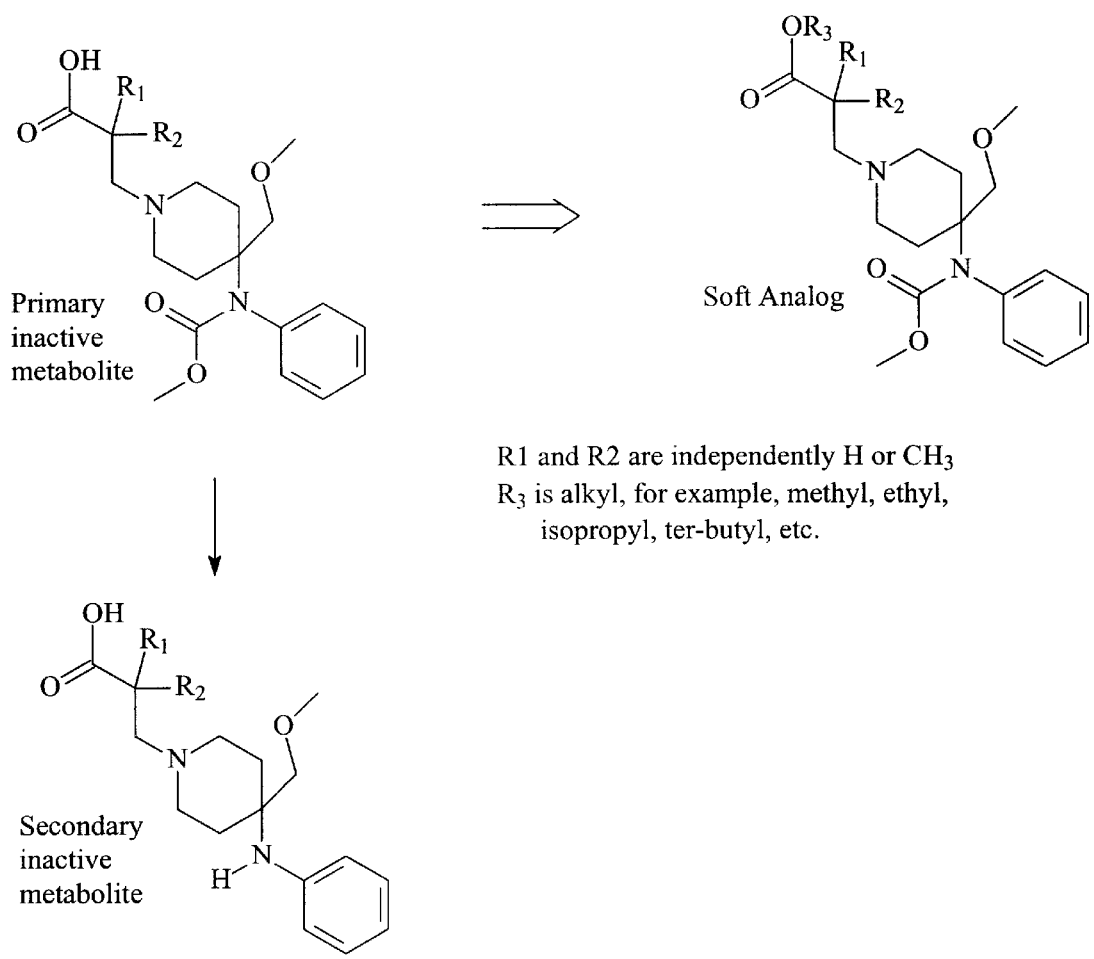
Figure 8:
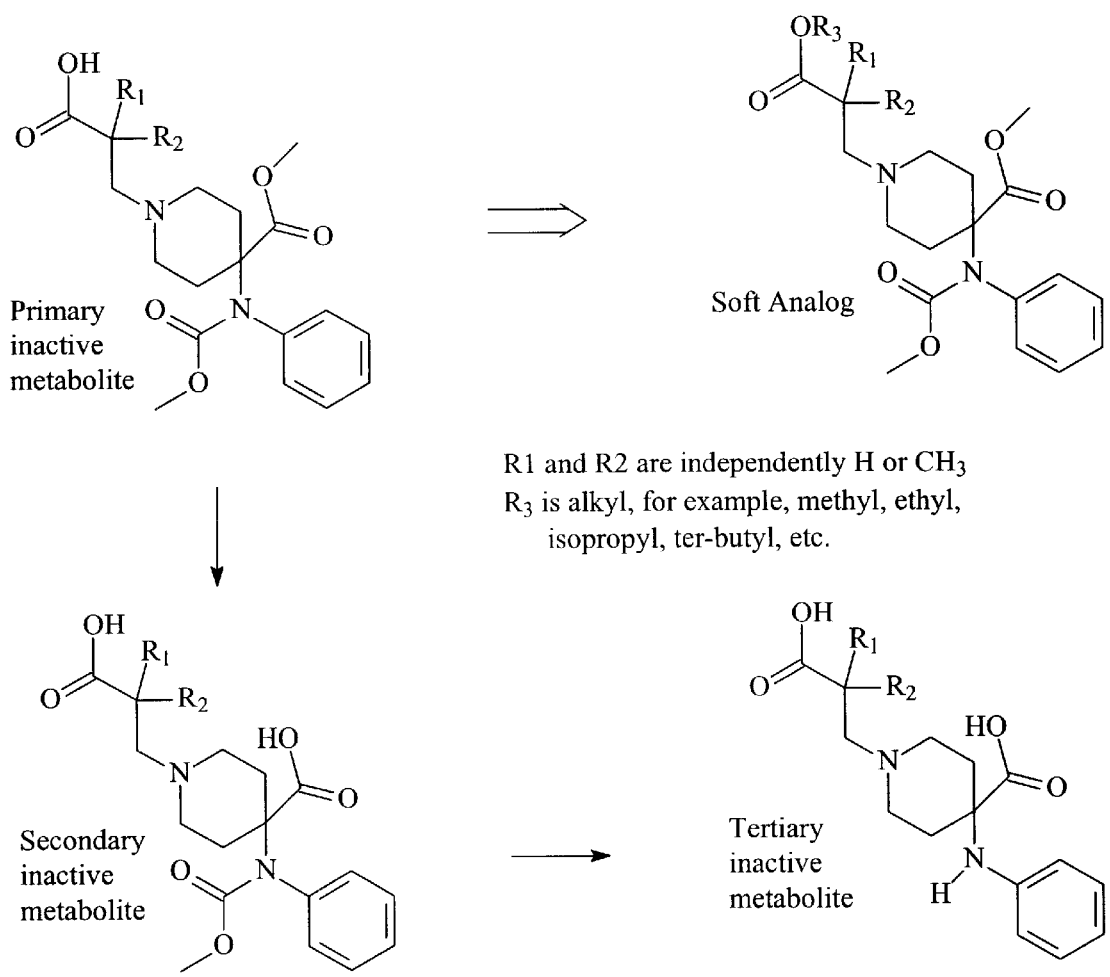
Figure 9:
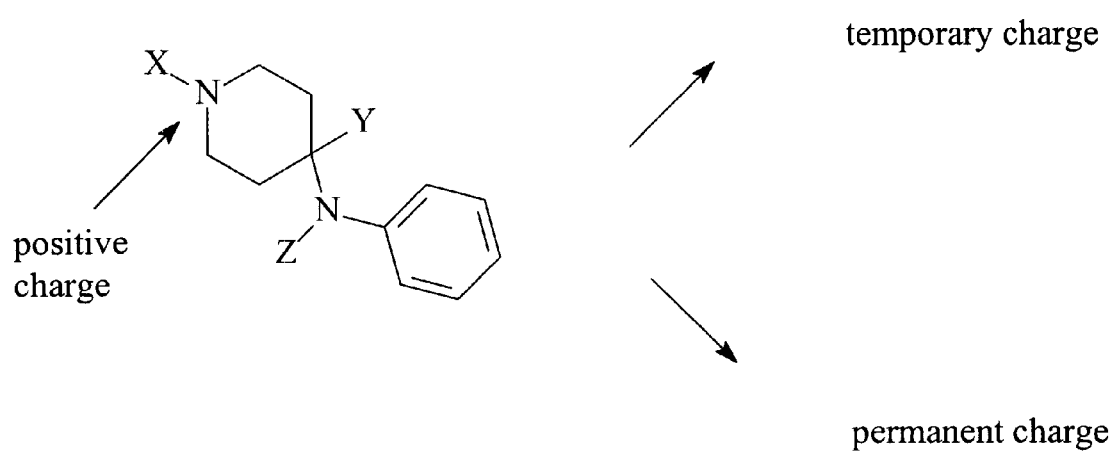
FIG. 9 shows that a positive charge can be introduced on the piperidine nitrogen.
Figure 10:
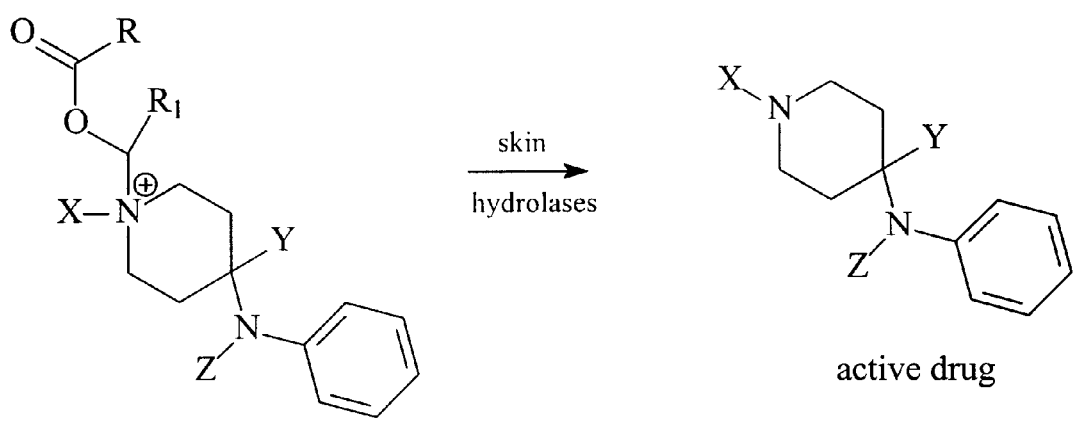
FIG. 10 shows that the positive charge can be reversible.
Figure 11:
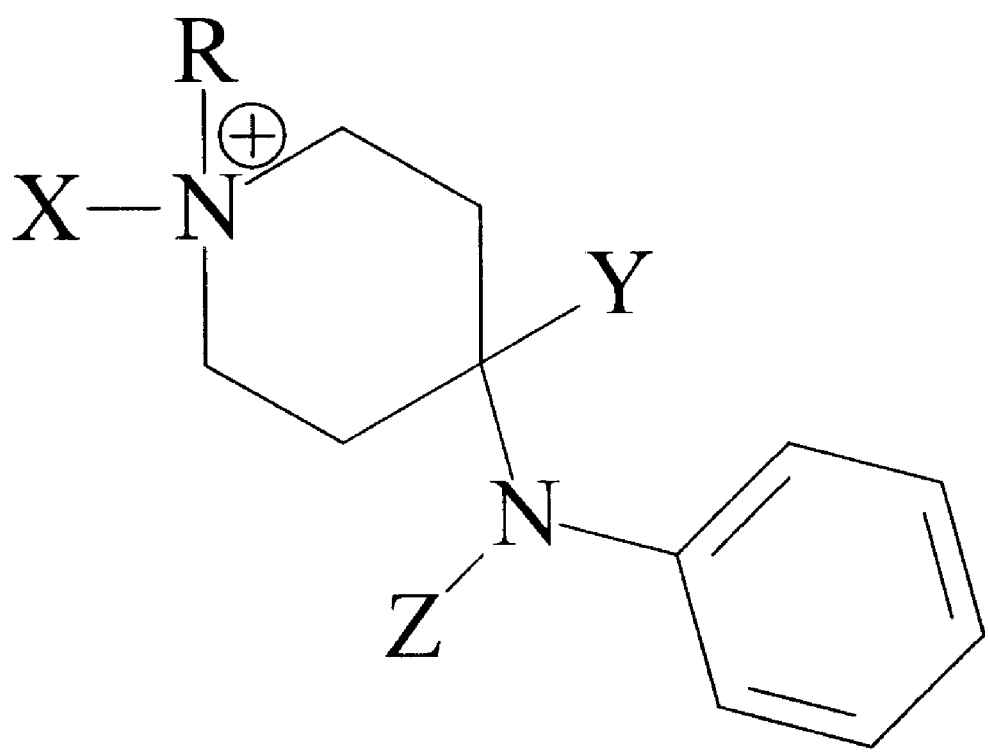
FIG. 11 shows that the positive charge can be permanent.
Figure 12:
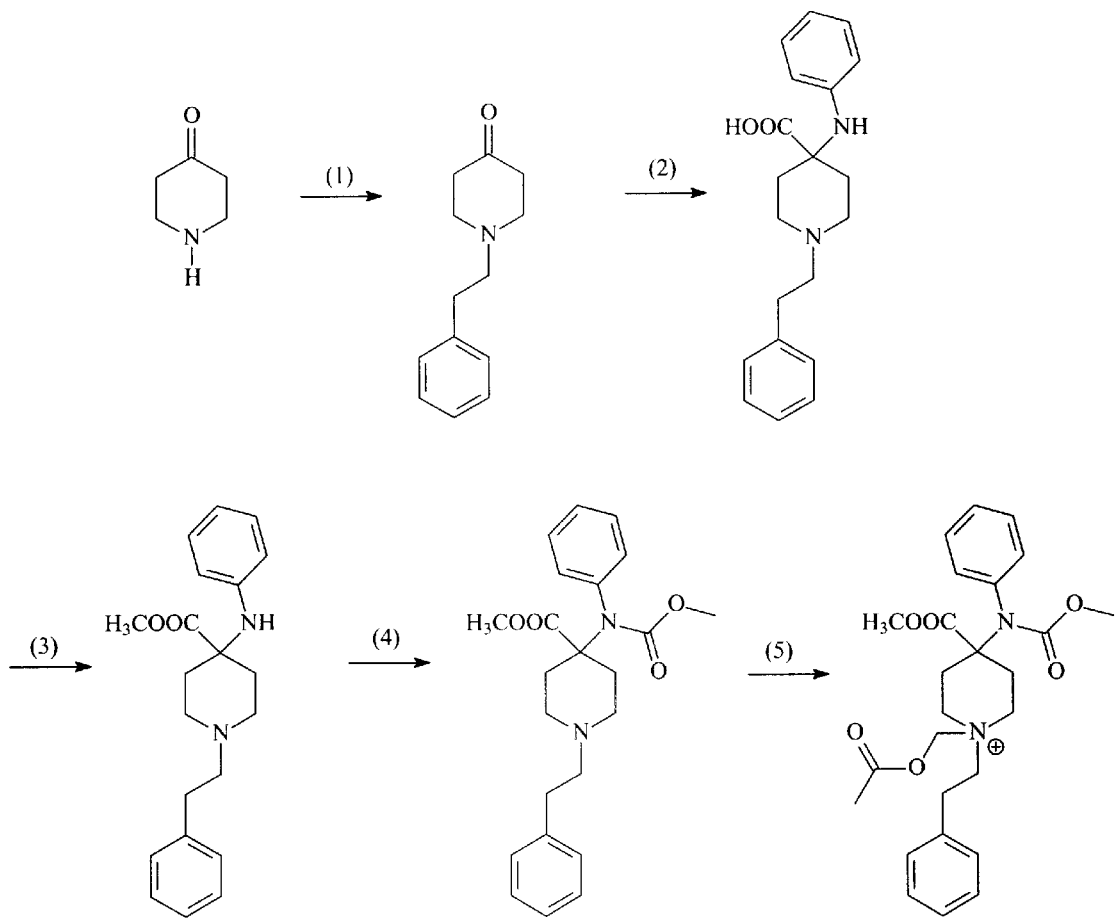
FIG. 12 shows a synthetic scheme.

Fentanyl, alfentanyl, sufentanyl, and remifentanil are opioid analgesics that are marketed in the United States (FIG. 1). As shown in FIG. 2, the opioid molecule has several potential sites (indicated by arrows) where soft chemistry can be applied according to the subject invention to modify the molecule. These sites are either on the piperidine nitrogen, or at the 4-position of the piperidine ring. There are at least six (6) different retrometabolic approaches leading to a soft opioid molecule, i. e., an active molecule having opioid properties and which is deactivated by hydrolytic enzymes to a primary inactive metabolite. These approaches are described in FIGS. 3–8. A positive charge can be introduced on the piperidine nitrogen (FIG. 9). This charge makes possible delivery by iontopheresis. The charge can be reversible (FIG. 10) or can be permanent (FIG. 11). A synthetic scheme for these molecules is described in FIG. 12. The groups designated X, Y, and Z in these figures are defined in accordance with the specific compounds exemplified herein.

Reference herein to alkyl includes $C_{1-8}$ straight or branched alkyl groups.

Adverse drug—drug interactions (DDI), elevation of liver function test (LFT) values, and QT prolongation leading to torsades de pointes (TDP) are three major reasons why drug candidates fail to obtain FDA approval. All these causes are, to some extent metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The compounds of this invention have one or more of the following characteristics or properties:

1. Compounds of the invention are metabolized both by CYP450 and by a non-oxidative metabolic enzyme or system of enzymes;
2. Compounds of the invention have a short (up to four (4) hours) non-oxidative metabolic half-life;

3. Oral bioavailability of the compounds is consistent with oral administration using standard pharmaceutical oral formulations; however, the compounds, and compositions thereof, can also be administered using any delivery system that produces constant and controllable blood levels over time;

4. Compounds according to the invention contain a hydrolysable bond that can be cleaved non-oxidatively by hydrolytic enzymes;

5. Compounds of the invention can be made using standard techniques of small-scale and large-scale chemical synthesis;

6. The primary metabolites of compounds of this invention results from the non-oxidative metabolism of the compounds;

7. The primary metabolites, regardless of the solubility properties of the parent drug, is, or are, soluble in water at physiological pH and have, as compared to the parent compound, a significantly reduced pharmacological activity;

8. The primary metabolites, regardless of the electrophysiological properties of the parent drug, has, or have, negligible inhibitory activity at the $IK_R$ (HERG) channel at normal therapeutic concentration of the parent drug in plasma (e.g., the concentration of the metabolite must be at least five times higher than the normal therapeutic concentration of the parent compound before activity at the $IK_R$ channel is observed);

9. Compounds of the invention, as well as the metabolites thereof, do not cause metabolic DDI when co-administered with other drugs;

10. Compounds of the invention, as well as metabolites thereof, do not elevate LFT values when administered alone.

In some embodiments, the subject invention provides compounds have any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds have any combination of five to 10 of the above-identified characteristics or properties. In a preferred embodiment the compounds of the invention have all ten characteristics or properties.

In various embodiments, the primary metabolites of the inventive compounds, regardless of the electrophysiological properties of the parent drug, has, or have, negligible inhibitory activity at the $IK_R$ (HERG) channel at normal therapeutic concentrations of the drug in plasma. In other words, the concentration of the metabolite must be at least five times higher than the normal therapeutic concentration of the parent compound before activity at the $IK_R$ channel is observed. Preferably, the concentration of the metabolite must be at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

The invention also concerns methods for treating pain in a patient by administering a compound of the invention to a person in need of such treatment. Preferably, the compound is administered by transdermal delivery means. A fentanyl analog of the present invention having a short half-life in blood can be delivered by a transdermal system in which the delivery rate closely matches clearance of the drug from the bloodstream.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, $54^{th}$ Ed., Medical Economics Company, Montvale, N.J., 2000).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The compounds of the subject invention can be used to treat humans and other animals. All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. An opioid compound having a structure selected from the group consisting of:

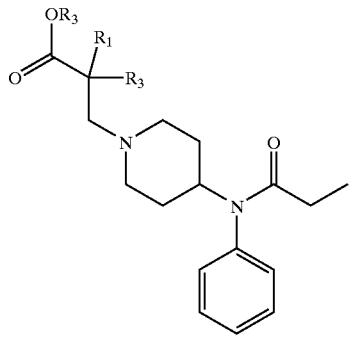

wherein, $R_1$ and $R_2$ are, independently, H or $CH_3$ and $R_3$ is alkyl;

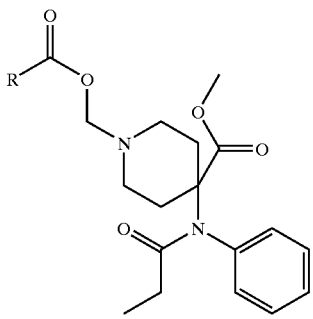

wherein, R=alkyl; aryl; methoxy; alkyloxy; or aryloxy;

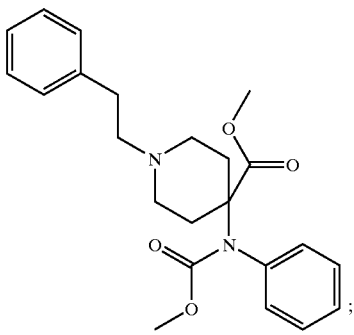

;

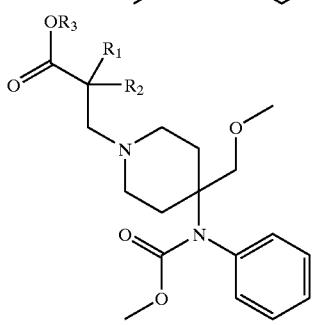

wherein, $R_1$ and $R_2$ are, independently, H or $CH_3$ and $R_3$ is alkyl; and

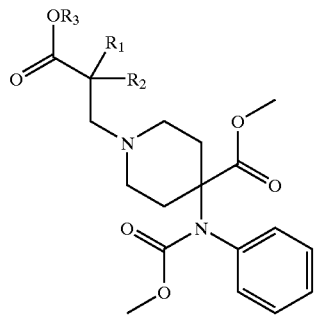

wherein, $R_1$ and $R_2$ are, independently, H or $CH_3$ and $R_3$ is alkyl.

2. The opioid compound, according to claim 1, wherein said compound has the following structure:

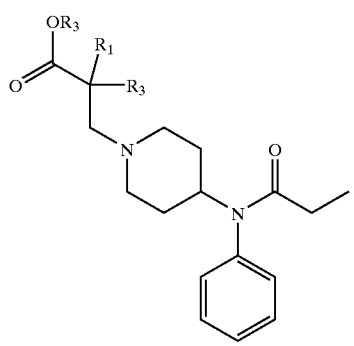

wherein, $R_1$ and $R_2$ are, independently, H or $CH_3$ and $R_3$ is alkyl.

3. The opioid compound, according to claim 1, wherein said compound has the following structure:

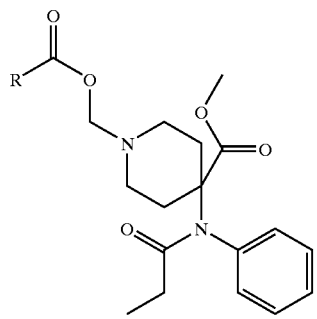

wherein, R=alkyl; aryl; methoxy; alkyloxy; or aryloxy.

4. The opioid compound, according to claim 1, wherein said compound has the following structure:

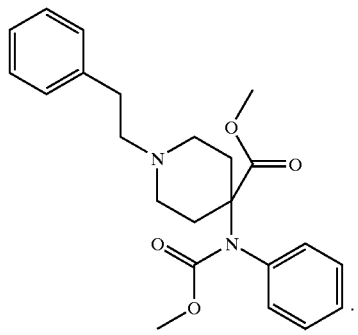

5. The opioid compound, according to claim 1, wherein said compound has the following structure:

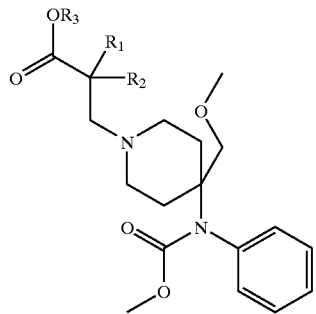

wherein, $R_1$ and $R_2$ are, independently, H or $CH_3$ and $R_3$ is alkyl.

6. The opioid compound, according to claim 1, wherein said compound has the following structure:

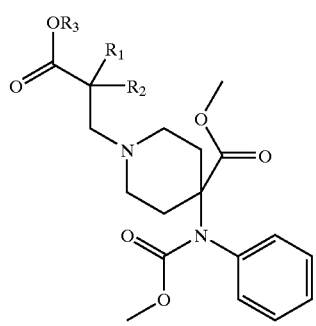

wherein, $R_1$ and $R_2$ are, independently, H or $CH_3$ and $R_3$ is alkyl.

7. A pharmaceutical composition comprising an opioid compound having a structure selected from the group consisting of:

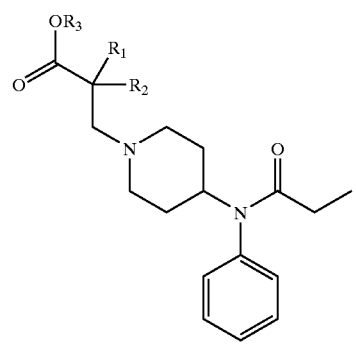

wherein, $R_1$ and $R_2$ are, independently, H or $CH_3$ and $R_3$ is alkyl;

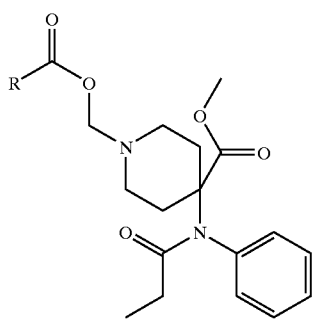

wherein, R=alkyl; aryl; methoxy; alkyloxy; or aryloxy;

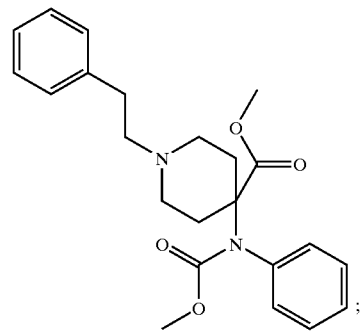

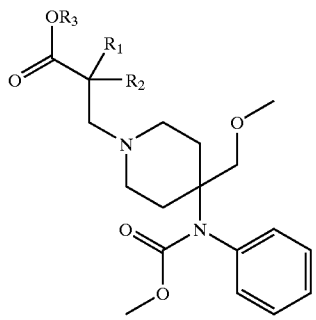

wherein, $R_1$ and $R_2$ are, independently, H or $CH_3$ and $R_3$ is alkyl; and

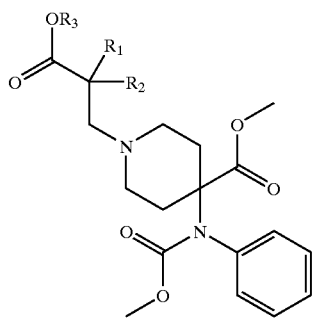

wherein, $R_1$ and $R_2$ are, independently, H or $CH_3$ and $R_3$ is alkyl.

8. The composition, according to claim 7, wherein said compound has the following structure:

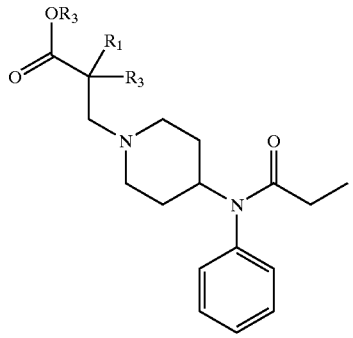

wherein, $R_1$ and $R_2$ are, independently, H or $CH_3$ and $R_3$ is alkyl.

9. The composition, according to claim 7, wherein said compound has the following structure:

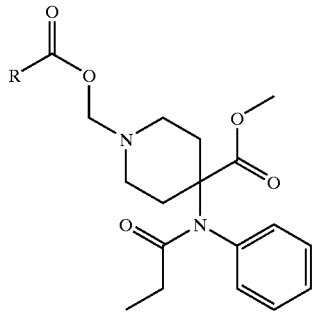

wherein, R=alkyl; aryl; methoxy; alkyloxy; or aryloxy.

10. The composition, according to claim 7, wherein said compound has the following structure:

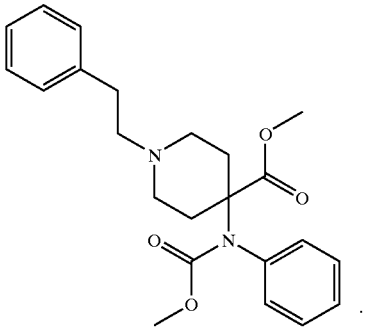

11. The composition, according to claim 7, wherein said compound has the following structure:

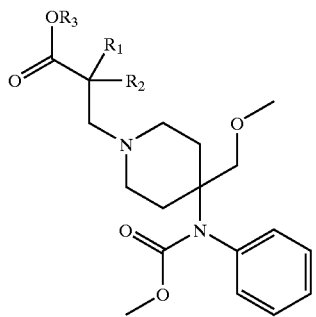

wherein, $R_1$ and $R_2$ are, independently, H or $CH_3$ and $R_3$ is alkyl.

12. The composition, according to claim 1, wherein said compound has the following structure:

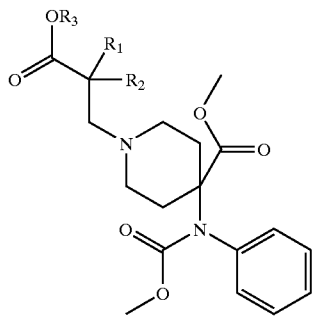

wherein, $R_1$ and $R_2$ are, independently, H or $CH_3$ and $R_3$ is alkyl.

13. A method for treating pain wherein said method comprises administering to a patient in need of such treatment an opioid compound having

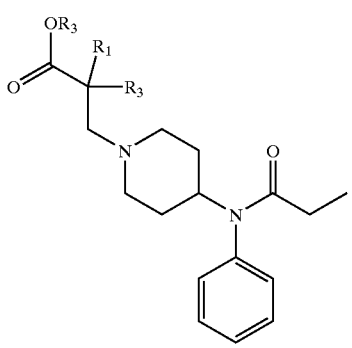

wherein, $R_1$ and $R_2$ are, independently, H or $CH_3$ and $R_2$ is alkyl;

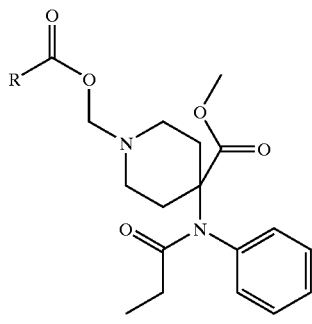

wherein, R=alkyl; aryl; methoxy; alkyloxy; or aryloxy;

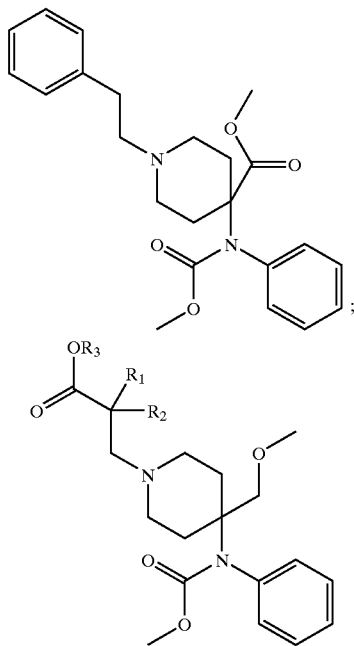

wherein, $R_1$ and $R_2$ are, independently, H or $CH_3$ and $R_3$ is alkyl; and wherein, $R_1$ and $R_2$ are, independently, H or $CH_3$ and $R_3$ is alkyl.

14. The method, according to claim 13, wherein said compound has the following structure:

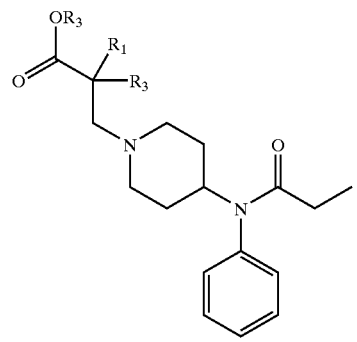

wherein, $R_1$ and $R_2$ are, independently, H or $CH_3$ and $R_3$ is alkyl.

15. The method, according to claim 13, wherein said compound has the following structure:

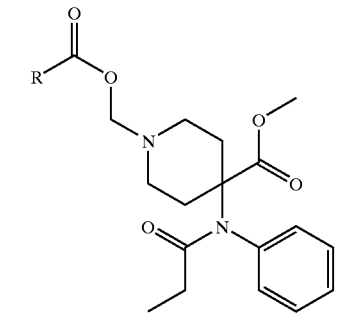

wherein, R=alkyl; aryl; methoxy; alkyloxy or aryloxy.

16. The method, according to claim 13, wherein said compound has the following structure:

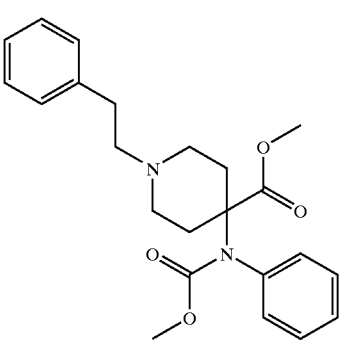

17. The method, according to claim 13, wherein said compound has the following structure:

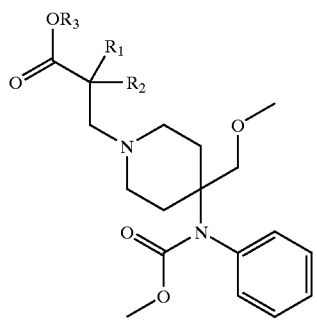
wherein, $R_1$ and $R_2$ are, independently, H or $CH_3$ and $R_3$ is alkyl.
18. The method, according to claim 13 wherein said compound has the following structure:
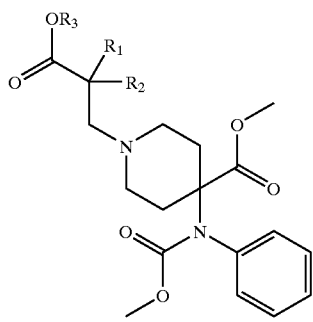
wherein, $R_1$ and $R_2$ are, independently, H or $CH_3$ and $R_3$ is alkyl.
19. The method, according to claim 13, wherein said patient is a human.
* * * * *

UNITED STATES PATENT AND TRADEMARK OFFICE
CERTIFICATE OF CORRECTION

PATENT NO. : 6,686,377 B2
DATED : February 3, 2004
INVENTOR(S) : Druzgala

It is certified that error appears in the above-identified patent and that said Letters Patent is hereby corrected as shown below:

Column 10,
Line 49, "...compound having" should read -- ...compound having a structure selected from the group consisting of: --
Line 66, "...H or $CH_3$ and $R_2$ is alkyl;" should read -- "...H or $CH_3$ and $R_3$ is alkyl; --

Column 12,
Line 6, (in structure), "$R_3$" should read -- $R_2$ --
Line 43, "...alkyloxy or aryloxy." should read -- ...alkloxy; or aryloxy. --

Signed and Sealed this

Twenty-ninth Day of June, 2004

JON W. DUDAS
*Acting Director of the United States Patent and Trademark Office*